(12) United States Patent
Harrington et al.

(10) Patent No.: US 9,393,134 B2
(45) Date of Patent: Jul. 19, 2016

(54) LASER SYSTEM AND PROCESSING CONDITIONS FOR MANUFACTURING BIOABSORBABLE STENTS

(71) Applicant: Abbott Cardiovascular Systems Inc., Santa Clara, CA (US)

(72) Inventors: Joel Harrington, Redwood City, CA (US); Ryan Vaughan, Mountain View, CA (US); Kevin Jow, San Mateo, CA (US); William Pippey, San Jose, CA (US); Yung-Ming Chen, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/171,686

(22) Filed: Feb. 3, 2014

(65) Prior Publication Data
US 2014/0155985 A1    Jun. 5, 2014

Related U.S. Application Data

(62) Division of application No. 12/797,950, filed on Jun. 10, 2010, now Pat. No. 8,679,394.

(51) Int. Cl.
*A61F 2/90* (2013.01)
*A61F 2/91* (2013.01)
(Continued)

(52) U.S. Cl.
CPC ... *A61F 2/90* (2013.01); *A61F 2/91* (2013.01); *B23K 26/0624* (2015.10); *B23K 26/0635* (2013.01); *B23K 26/402* (2013.01); *B23K 26/4065* (2013.01); *B23K 2203/42* (2015.10)

(58) Field of Classification Search
CPC ............... A61F 2/82; A61F 2/86; A61F 2/90; A61F 2/91; A61F 2/915
USPC .......................................................... 623/1.15
See application file for complete search history.

(56) References Cited

U.S. PATENT DOCUMENTS

| 2005/0252893 A1 | 11/2005 | Shapovalov et al. |
| 2006/0229711 A1 | 10/2006 | Yan et al. |

(Continued)

FOREIGN PATENT DOCUMENTS

| EP | 0 842 729 A1 | 5/1998 |
| WO | WO/2007/081550 A1 | 7/2007 |

(Continued)

OTHER PUBLICATIONS

European Search Report for EP 15159720, mailed Oct. 19, 2015, 8 pgs.

(Continued)

*Primary Examiner* — Christina Johnson
*Assistant Examiner* — Xue Liu
(74) *Attorney, Agent, or Firm* — Squire Patton Boggs (US) LLP

(57) ABSTRACT

The present invention involves laser machining polymer substrates to form a stent with laser parameters that minimize damage to the substrate in a surface region adjacent to the machined edge surface. The wavelength and pulse width are selected for this unique application and they can be controlled to minimize the surface modifications (such as voids, cracks which are induced by the laser-material interaction) which contribute to the variation in mechanical properties with distance from the edge surface, bulk mechanical properties, or a combination thereof.

13 Claims, 9 Drawing Sheets

(51) Int. Cl.
  *B23K 26/06* (2014.01)
  *B23K 26/40* (2014.01)

(56) References Cited

U.S. PATENT DOCUMENTS

| | | | |
|---|---|---|---|
| 2007/0038290 A1 | 2/2007 | Huang et al. | |
| 2007/0142903 A1 | 6/2007 | Dave | |
| 2007/0272555 A1 | 11/2007 | Baird | |
| 2007/0283552 A1 | 12/2007 | Gale et al. | |
| 2008/0269870 A1 | 10/2008 | Ruuttu et al. | |
| 2009/0216316 A1 | 8/2009 | Wang et al. | |
| 2010/0093946 A1* | 4/2010 | Thatcher et al. | 525/411 |

FOREIGN PATENT DOCUMENTS

| | | |
|---|---|---|
| WO | WO/2007/006043 A2 | 11/2007 |
| WO | WO 2009/155206 A2 | 12/2009 |

OTHER PUBLICATIONS

China Office Action and Search Report for CN Appln. No. 20118002663.9 mailed Jun. 27, 2014, 11 pages.

Japan Office Action for Japan Application No. 2013-514326, mailed Mar. 24, 2015, 8 pages.

Bauer et al., "Development of an industrial femtosecond laser micromachining system", Proc. SPIE 4633, Commercial and Biomedical Applications of Ultrafast and Free-Electron Lasers, 128, Apr. 5, 2002, 8 pages.

Fischer-Cripps, "Nanoindentation", Chapter 2 Nanoindentation Testing, Springer, 2002, New York, pp. 20-22.

Plitzko et al., "Science of Microscopy", Chapter 7 Cryoelectron Tomography, Springer, 2007, New York, vol. 1, pp. 552-554.

Hermann et al, "Improved picosecond laser radiation for micromachining, Paper M1003", ICALEO, Congress Proceedings, Laser Microprocessing Conference, 2006, pp. 304-310.

Huttunen et al., "Nano-, pico- and femtosecond laser machining of bioabsorbable polymers and biomedical composites", ICALEO, Congress Proceeding, Laser Microprocessing Conference, 2008, pp. 415-420.

Klimt, "Micromachining with industrial picosecond lasers", Laser Micro Machining, Jan. 2007, No. 1, pp. 40-43.

Lanzer, "Mastering Endovascular Techniques—A Guide to Excellence", Lippincott Williams and Wilkins, pp. 132-134, 2006.

Dahotre et al., Laser Fabrication and Machining of Materials, Springer, 2008, New York, pp. 179-180.

Nebel et al, "Generation of tailored picosecond-pulse-trains for micromachining", Proc. Of SPIE, 2006, vol. 6108, 610-812, pp. 1-8.

Notice of opposition and Opposition as filed towards European Patent No. EP 2580020, mailed Jan. 29, 2016, 27 pages.

RAPID data sheet, Industrial, High Repetition Rate Picosecond Laser, Lumber Laser GmbH, 2006, 7 pages.

* cited by examiner

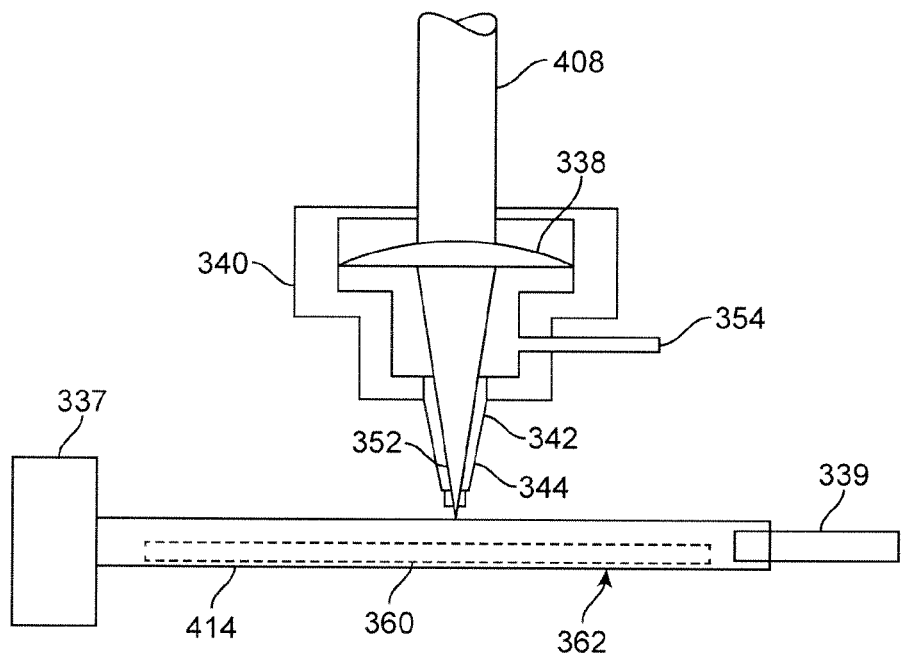
FIG. 3
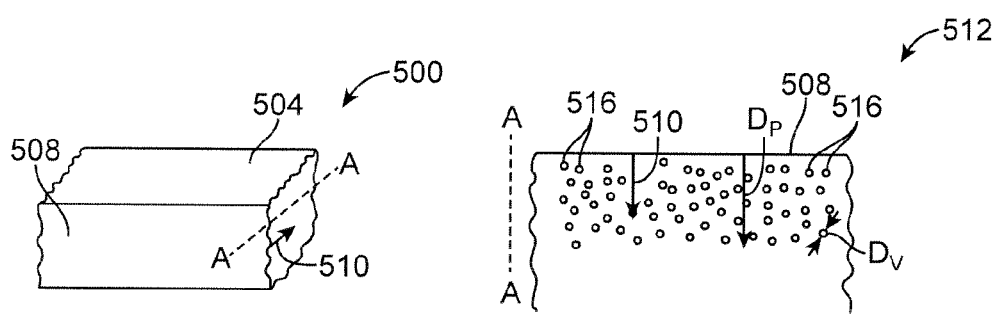
FIG. 4A
FIG. 4B

LASER SYSTEM AND PROCESSING CONDITIONS FOR MANUFACTURING BIOABSORBABLE STENTS

This application is a division of application Ser. No. 12/797,950 filed on Jun. 10, 2010 and is incorporated by reference herein for any reason.

BACKGROUND OF THE INVENTION

1. Field of the Invention

This invention relates to laser machining tubing to form stents.

2. Description of the State of the Art

This invention relates to laser machining of devices such as stents. Laser machining refers to removal of material accomplished through laser and target material interactions. Generally speaking, these processes include laser drilling, laser cutting, and laser grooving, marking or scribing. Laser machining processes transport photon energy into a target material in the form of thermal energy or photochemical energy. Material is removed by melting and blow away, or by direct vaporization/ablation.

When a substrate is laser machined energy is transferred into the substrate. As a result, a region beyond the cutting edge is modified by the energy, which affect the properties in this region. In general, the changes in properties are adverse to the proper functioning of a device that is being manufactured. Therefore, it is generally desirable to reduce or eliminate energy transfer beyond removed material, thus reducing or eliminating the extent of modification and size of the region affected.

One of the many medical applications for laser machining includes fabrication of radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, the stent must possess adequate radial strength and rigidity. Radial strength is the ability of a stent to resist radial compressive forces. Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. The stent should have sufficient resistance to fracture so that stent performance is not adversely affected during the crimping, expansion, and cycling loading.

Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Stents have been made of many materials such as metals and polymers, including biodegradable polymeric materials. Biodegradable stents are desirable in many treatment applications in which the presence of a stent in a body may be necessary for a limited period of time until its intended function of, for example, achieving and maintaining vascular patency and/or drug delivery is accomplished.

Stents can be fabricated by forming patterns on tubes or sheets using laser machining. Even though the basic laser-material interaction is similar, there are certain aspects among types of materials (such as metals, plastics, glasses, and ceramics), i.e. different absorption characteristics. To produce the desired results, it is critical in choosing a suitable wavelength. Once a suitable wavelength is selected, it is the combination of pulse energy and pulse duration that define the optimal process condition for the type of material. The properties of biodegradable polymers like PLLA and PLGA tend to be very sensitive to energy transfer such as that from laser machining. There are great efforts needed in understanding the laser parameters and laser-material interaction to help select a laser system and define processing parameters enabling faster laser machining of biodegradable stents which minimize the adverse effects on the properties.

SUMMARY OF THE INVENTION

Various embodiments of the present invention include a method of laser machining a substrate to form a stent, comprising: providing a thin-walled polymer substrate; laser machining the thin-walled polymer substrate with a laser beam with a pulse width and wavelength that can cut through the wall of the substrate to form structural elements having a machined edge surface, wherein the laser beam modifies the substrate in a surface region adjacent to the machined edge surface in much less degree, wherein the modifications include voids, cracks that contribute to the variation in modulus of the polymer with distance from the edge surface, or a combination thereof, and selecting the pulse width and wavelength so that the voids or cracks are present at no greater than a depth of 2 microns or the modulus converges at no greater than 4 microns.

Additional embodiments of the present invention include a method of laser machining a substrate to form a stent, comprising: providing a thin-walled PLLA polymer substrate; laser machining the thin-walled PLLA polymer substrate with a laser beam to cut through the wall to form structural elements having a machined edge surface, wherein the pulse width and wavelength of the laser beam are within the green range and the pulse width is 1-10 ps.

Further embodiments of the present invention include a polymer stent body, comprising: a plurality of interconnected structural elements formed by laser machining a thin-walled PLLA polymer substrate with a laser beam that cuts through the wall to form the structural elements, wherein the structural elements have sidewalls corresponding to a machined edge surface, wherein a surface region adjacent to the sidewalls has damage caused by interaction of the laser beam with the substrate, wherein the damage comprises voids or cracks dispersed in the surface region to a depth of 2 microns or less from the edge surface.

BRIEF DESCRIPTION OF THE DRAWINGS

FIG. 3 depicts a close-up axial view of a region where a laser beam interacts with a tube.

FIG. 4A depicts a portion of a strut or structural element formed by laser machining a substrate.

FIG. 4B depicts a cross-section of a portion of a strut normal to a machined edge surface.

DETAILED DESCRIPTION OF THE INVENTION

Embodiments of the present invention relate to methods of laser machining of polymer substrates to manufacture a stent. More specifically, these embodiments relate to selecting and implementing a laser system and parameters that reduce or eliminate adverse effects of the laser on the polymer and which maximize the preservation of the functional properties of the material, such as the surface and bulk properties of the polymer material.

In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency.

Figure 1:
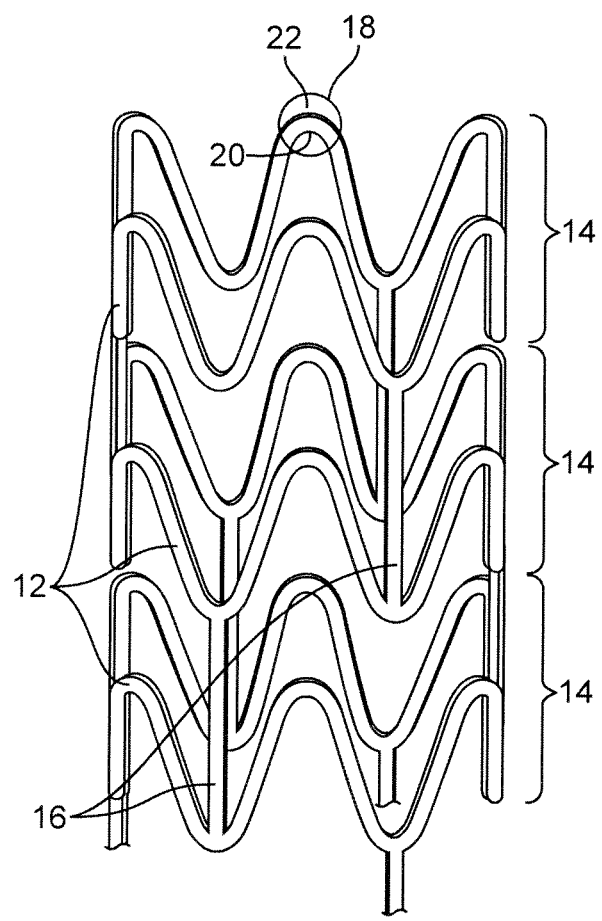
FIG. 1 depicts a stent.

An exemplary structure of a stent is shown in FIG. 1. FIG. 1 depicts a stent 10 which is made up of struts 12. Stent 10 has interconnected cylindrical rings 14 connected by linking struts or links 16. The embodiments disclosed herein are not limited to fabricating stents or to the stent pattern illustrated in FIG. 1. The embodiments are easily applicable to other stent patterns and other devices. The variations in the structure of patterns are virtually unlimited. The outer diameter of a fabricated stent (prior to crimping and deployment) may be between 0.2-5.0 mm. For coronary applications, a fabricated stent diameter is 2.5-5 mm. The length of the stents may be between about 6-12 mm or more depending on the application.

The present embodiments are particular relevant to laser machining polymer substrates to form stents, however, the methods may be applicable to other materials such as metals and ceramics or composite materials composed of combinations of polymer, metal, and ceramic.

Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body. In addition, a medicated stent may be fabricated by coating the surface of the stent with an active agent or drug, or a biodegradable polymer carrier including an active agent or drug. The drug coating is typically applied to the stent body or scaffolding after being formed by laser machining. The coating is typically much thinner than the struts of the scaffolding, for example, the coating can be 1-5 microns in thickness while the struts are typically greater than 100 microns in thickness, for example, 140-160 microns thick.

Figure 2:
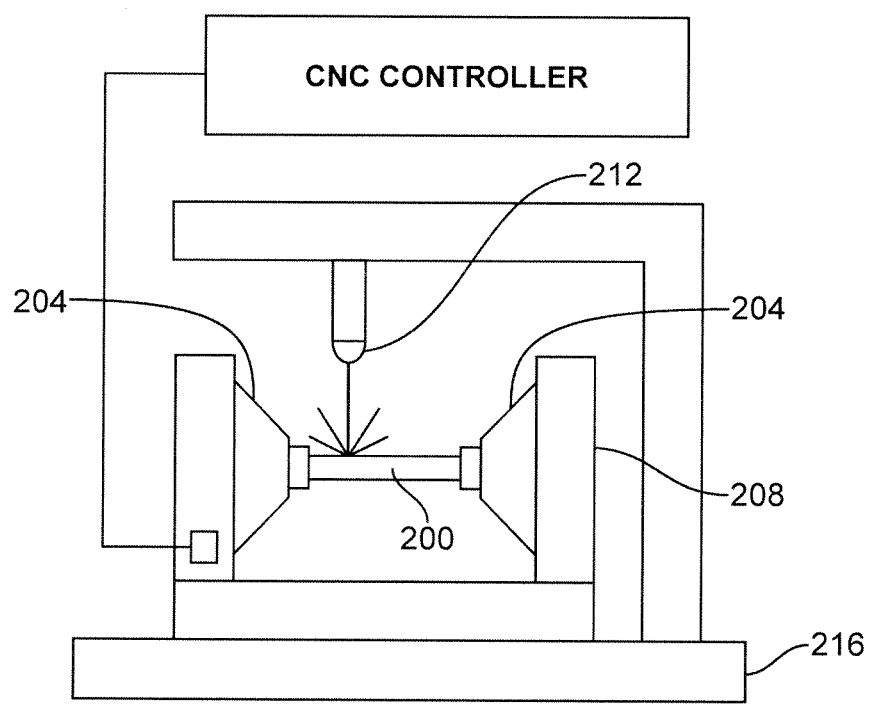
FIG. 2 depicts a machine-controlled system for laser machining a tube.
Figure 5:
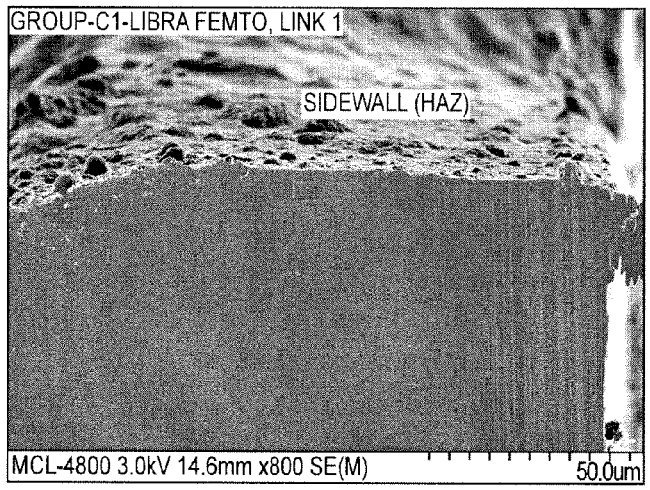
FIGS. 5-8 show SEM images of the surface region adjacent to a laser machined edge surface for combinations of pulse width and wavelength.
Figure 6:
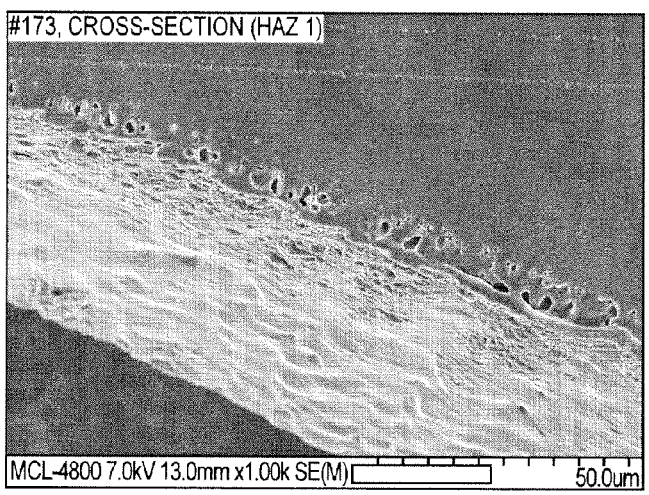
Figure 7:
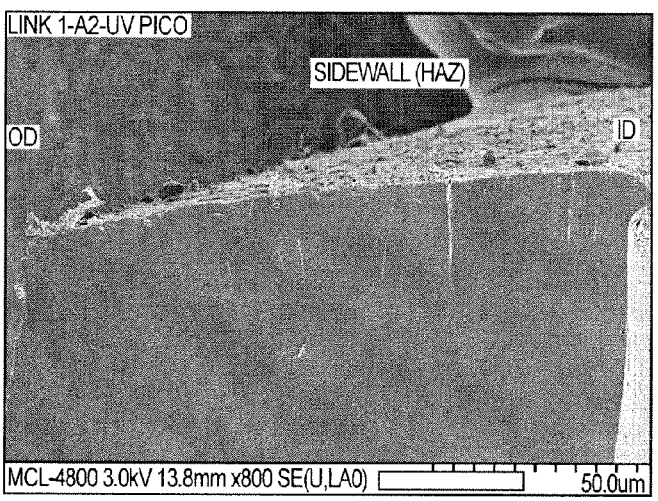
Figure 8:
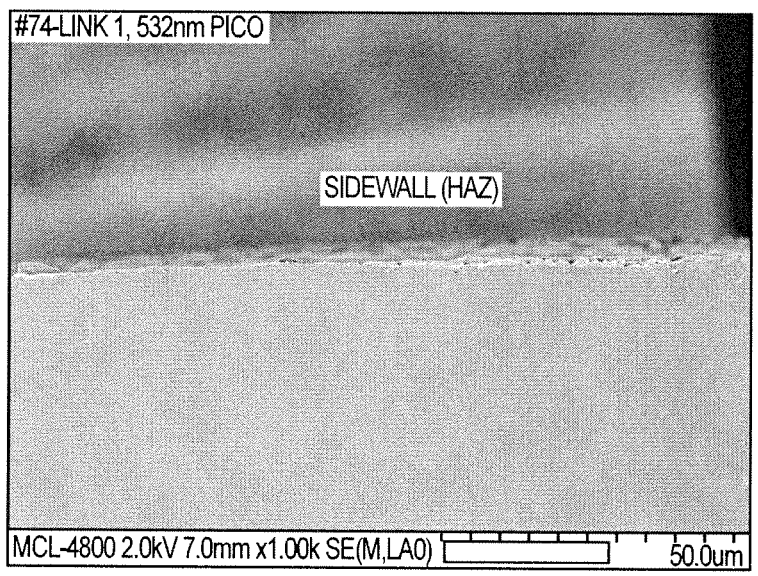

An implantable medical device, such as a stent, can be fabricated by laser machining a construct or substrate to form the device. Material is removed from selected regions of the construct which results in formation of the structure of the device. In particular, a stent may be fabricated by machining a thin-walled tubular member with a laser. Selected regions of the tubing may be removed by laser machining to obtain a stent with a desired pattern. Specifically, a laser beam can be scanned over the surface of a tubing or the tubing can be translated and rotated under the beam resulting in removal of a trench or kerf extending all the way through a wall of the tubing. When a starting and ending point of a kerf meet, the region surrounded by the kerf drops out or is removed by an assisting gas. FIG. 2 depicts an embodiment of a portion of a machine-controlled system for laser machining a tube. In FIG. 2, a tube 200 is disposed in a rotatable collet fixture 204 of a machine-controlled apparatus 208 for positioning tubing 200 relative to a laser 212. According to machine-encoded instructions, tube 200 is rotated and moved axially relative to laser 212 which is also machine-controlled. The laser selectively removes the material from the tubing resulting in a pattern cut into the tube. The tube is therefore cut into the discrete pattern of the finished stent.

FIG. 3 depicts a close-up view of a laser beam 408 interacting with a tube 414. Laser beam 408 is focused by a focusing lens 338 on tube 414. Tube 414 is supported by a controlled rotary collet 337 at one end and an optional tube support pin 339 at another end. A coaxial gas jet assembly 340 directs a cold gas jet or stream 342 that exits through a nozzle 344 that cools the machined surface as the beam cuts and ablates a substrate. The gas stream also helps to remove debris from the kerf and cool the region near the beam. Gas inlet is shown by an arrow 354. Coaxial gas jet nozzle 344 is centered around a focused beam 352. In some embodiments, the pressure of the supplied cooling gas is between 30 and 150 psi. An exemplary flow rate of the cooling gas is between 2 and 100 scfh. Exemplary cooling gases or process gases include helium, argon, nitrogen, oxygen, or a mixture of those gases.

Biodegradable polymers that may be suitable for stent scaffold applications include semi-crystalline polymers. In particular, these include polymers with a glass transition temperature (Tg) above human body temperature, which is about 37° C. The polymer substrate can be made in whole or in part from single or a combination of biodegradable polymers including, but not limited to, poly(L-lactide) (PLLA), polymandelide (PM), poly(DL-lactide) (PDLLA), polyglycolide (PGA), and poly(L-lactide-co-glycolide) (PLGA). For PLGA, it includes copolymer containing different molar ratios of L-lactide to glycolide, such as, 90:10, 75:25, 50:50, 25:75, and 10:90.

Several properties of a stent are essential for performing its function including, radial strength and fracture resistance or elongation at break. For example, adequate fracture resistance is required and crucial since the stent undergoes significant stress/strain in localized regions when the stent is crimped and deployed. The inside or concave regions 20, illustrated in FIG. 1, of the bends in the stent pattern or crowns 18 are subjected to high compressive stress and strain when the stent is crimped, but the outside or convex regions 22 of the crowns 18 are subjected to high compressive stress and strain when the stent is deployed. Thus, the stent during crimping and deployment is highly susceptible to cracking. Such cracking can lead to a loss of radial strength and potentially to premature and/or to a catastrophic failure of the stent. Therefore, it is essential that the mechanical properties of the polymeric stent can be maintained through the laser machining process.

To provide the stent with the desired properties, an additional process step can be introduced to enhance radial strength and fracture resistance to the pre-form, tubing, prior to the its lasing step. For example, fracture toughness can be greatly enhanced by controlling the size of crystalline domains and by optimizing an optimal amorphous/crystalline ratio for a semi-crystalline polymer; radial strength is also seen to be enhanced by preferential polymer chain alignment to the tube in the hoop direction. These desired microstructural properties can be tailored through a heated radial expansion step on the polymer tube above the Tg of the polymer. For example, for PLLA, a range 65-120° C. is preferred. On the contrary, localized heating to the substrate during laser cutting can result in modification of the desired microstructural properties, or damage to localized regions, which can result loss or reduction of the advantages provided by the processing of the tube.

Laser beam machining is one of most advanced non-contact type machining technology used in micro and nano-fabrication to fulfill the need in handling advanced engineering materials, stringent design requirements, intricate shape and unusual size. The present invention relates to lasers having pulse widths in a range of a picosecond ($=10^{-12}$) ("Picosecond" lasers) and having pulse widths in the range of a femtosecond ($=10^{-15}$). "Pulse width" refers to the duration of an optical pulse versus time. The duration can be defined in more than one way. Specifically, the pulse duration can be defined as the full width at half maximum (FWHM) of the optical power versus time. Picosecond and femtosecond lasers offer unique advantages for the removal of precise amount of materials with minimum thermal damage to the surrounding materials. In general, the picosecond lasers have pulse widths less than about 10 ps and the femtosecond lasers have pulse widths between 10 and 800 fs.

The two fundamental mechanisms involved in the laser ablation are believed to be photothermal and photochemical mechanism. In the photothermal mechanism the material is ablated by melting and vaporizing, whereas in photochemical mechanism the photo energy of light is used to break the chemical bonds of the polymer directly. The chemical bonds between atoms and molecules of the substrate are broken resulting in formation of gaseous species which are removed from the substrate.

Laser ablation of material from a substrate can occur by a thermal mechanism, a nonthermal mechanism, or a combination of both. Longer-pulse lasers, for example, remove material from a surface principally through a thermal mechanism. In a thermal mechanism, the laser energy that is absorbed results in a temperature increase at and near the absorption site and material is removed by conventional melting or vaporization. The disadvantage of machining by this mechanism is the occurrence of thermal damage of uncut substrate material. Such damage includes melting and thermal diffusion into a region or zone of material at the machining edge which results in modification of the properties of the substrate in the zone and cut quality problems.

Lasers with femtosecond pulse duration are of particular interest for ablating material recently as the pulse duration is less than the typical thermalization characteristic time (i.e., time to achieve thermal equilibrium) of a few picoseconds. Due to a much smaller thermal diffusion depth, it is considered as a completely or nearly completely nonthermal mechanism. A picosecond laser removes material mostly through a nonthermal mechanism, but also with some degree of thermal mechanism for some materials that is enough to cause some thermal damage to a substrate.

More specifically, the nonthermal mechanism involves optical breakdown in the target material which results in material removal. During optical breakdown of material, a very high free electron density, i.e., plasma, is produced through mechanisms such as multiphoton absorption and avalanche ionization. With optical breakdown, the target material is converted from its initial solid-state directly into fully ionized plasma on a time scale too short for thermal equilibrium to be established with a target material lattice. Therefore, there is negligible heat conduction beyond the region removed. As a result, there is negligible thermal stress or shock to the material beyond approximately 1 micron from the laser machined surface.

However, it is believed that it is not known in the prior art whether the nonthermal or photochemical mechanism can cause damage to the uncut substrate that adversely effects stent performance, in particular fracture resistance. Specifically, it is not clear that optical breakdown propagates or penetrates beyond the laser machined edge surface and causes damage within the substrate. It is also not known if such damage can influence properties that effect stent performance. Furthermore, the existent relationship of laser parameters in ablating polymeric materials such as wavelength, pulse energy, and pulse width of the laser beam to such potential damage is not known.

We have learned from our studies that although laser ablating PLLA material by a nonthermal mechanism by using a femtosecond laser has negligible thermal damage to the cut surface, the photochemical effect does cause damages (void and crack) under the surface region which is adjacent to the laser machined edge surface. These damages surely lower the stent performances. Therefore, it is critical in choosing a laser system and its processing parameters to fabricate polymer stents with minimum damages to the properties of stent such as fracture resistance.

The embodiments of the present invention include defining process parameters on a picosecond pulse laser system for making polymeric stents with preserved mechanical properties, such as radial strength, elongation at break, or fracture resistance. The laser parameters that are controlled include the pulse width and wavelength of the laser energy. The use of such parameters in laser machining can minimize damages arising from both thermal and nonthermal mechanisms. The embodiments further include implementing a laser system and its parameters on a laser machining used for making PLLA and PLGA-based substrates have minimum damage.

The inventors recognized that the extent and depth of the damage caused by the photochemical mechanism can be controlled by laser parameters such as pulse width and wavelength. In general, the inventors have recognized that in laser machining polymers there is a tradeoff between damage cause by a thermal and nonthermal mechanism. As discussed below, both thermal and nonthermal mechanisms (i.e., photochemical) cause damage to the substrate. Although the character of the damage is different, both can adversely effect stent performance. The laser parameters (e.g., pulse width and wavelength) can be adjusted to reduce the photochemical effects, but with some increase in the thermal mechanism.

To illustrate damages caused by shorter laser pulses, PLLA stent samples were made by using a laser system in the femtosecond and picosecond ranges. Void formation can be seen in the bulk of stent strut (below the surface). FIG. 4B shows voids are dispersed through the surface region of the cut edges.

It is believed that the high laser energy at the cut edge converts some of the inner solid mass into a volume of gas which results in the formation of voids or bubbles. The voids are dispersed within a region extending from the cut edge to a given depth and beyond this depth the voids dissipate. Such voids can act as stress concentrators that will facilitates fracture formation when stent strut is under stress, and thus, reduce fracture resistance and reduce elongation at break. In addition to voids, cracking in the same region is also commonly observed in the samples.

FIG. 4A depicts a portion of a strut or structural element 500 formed by laser machining a substrate. Strut 500 has an abluminal or outer surface (prior to machining the outer surface, e.g., of tube) and a laser machined edge surface 508. The depth into the substrate normal to edge surface 508 is shown by an arrow 510. FIG. 4B depicts a cross-section 512 of a portion of strut 500 normal to machined edge surface 500 along A-A. As shown by the cross-section, the substrate has voids or bubbles 516 with a diameter Dv that extend to a depth Dp.

Figure 9:
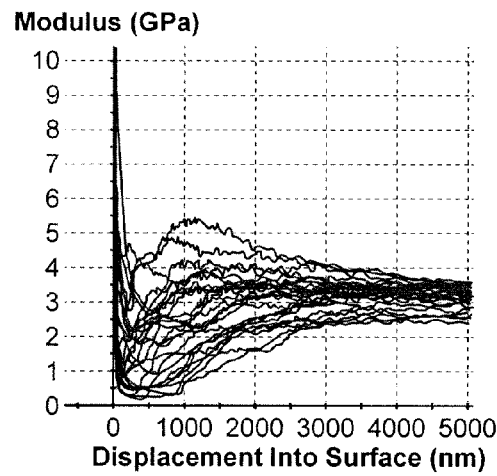
FIGS. 9-13 show the modulus vs. displacement into the surface of a laser machined edge for combinations of pulse width and wavelength.
Figure 10:
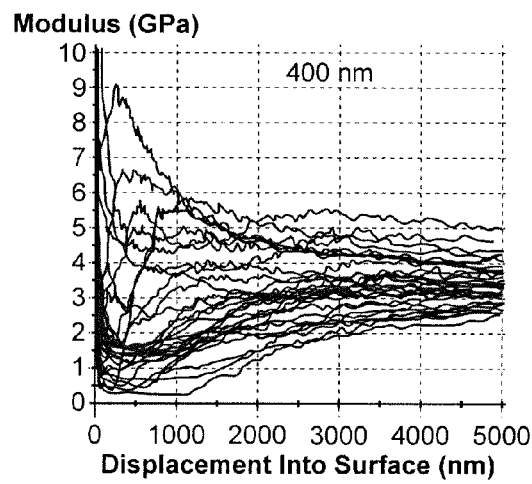
Figure 11:
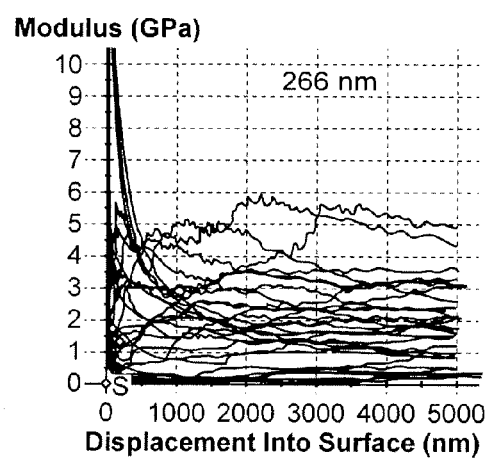
Figure 12:
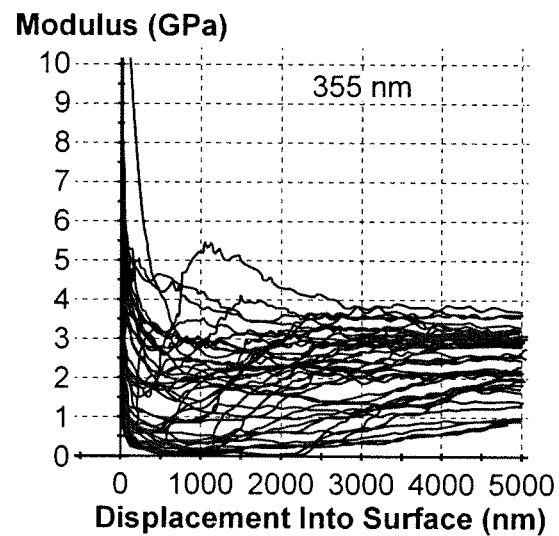
Figure 13:
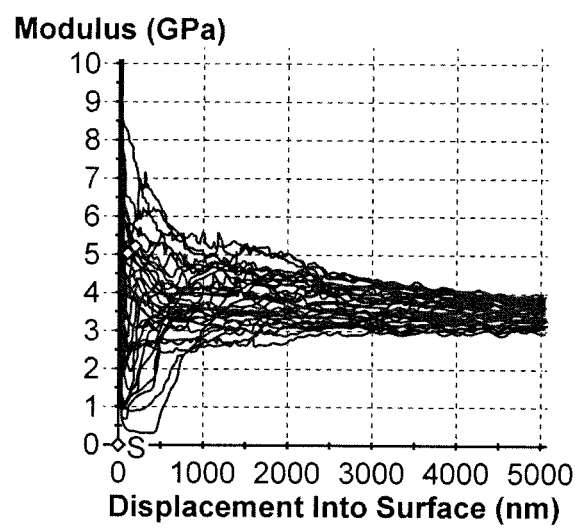
Figure 14:
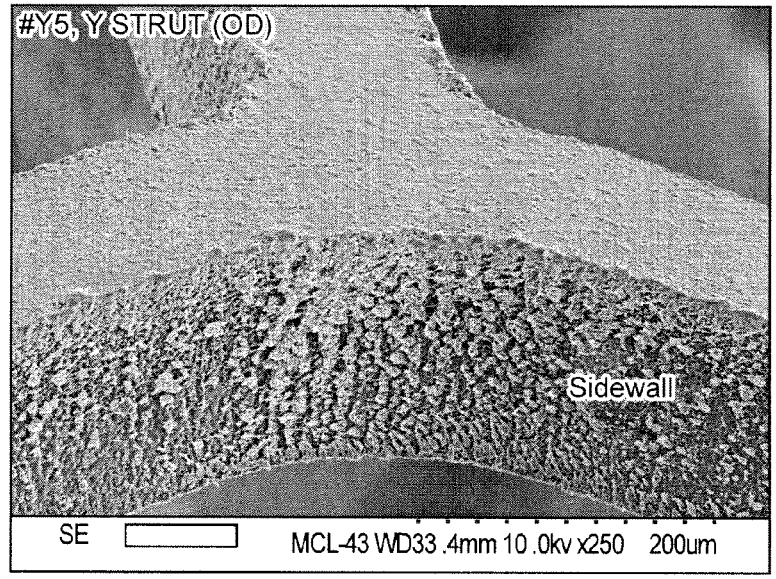
FIGS. 14-17 depict SEM images showing the sidewall surfaces of stents machined with different combinations of pulse widths and wavelengths.
Figure 15:
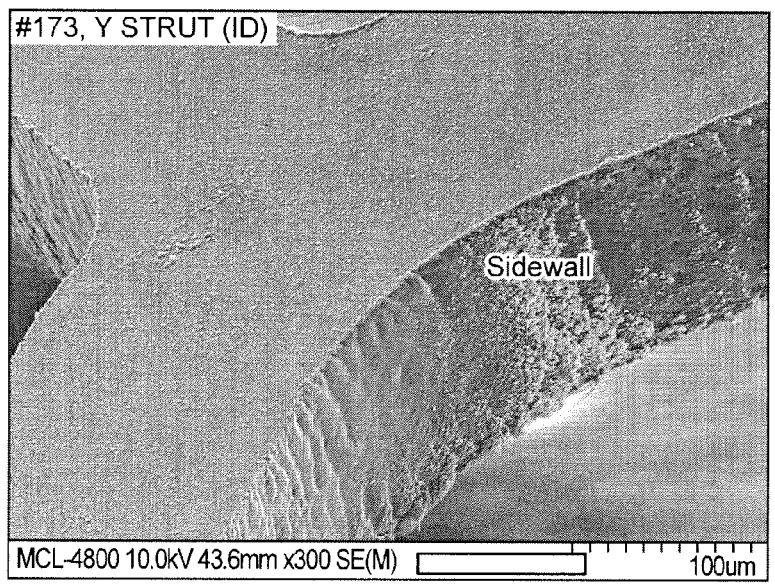
Figure 16:
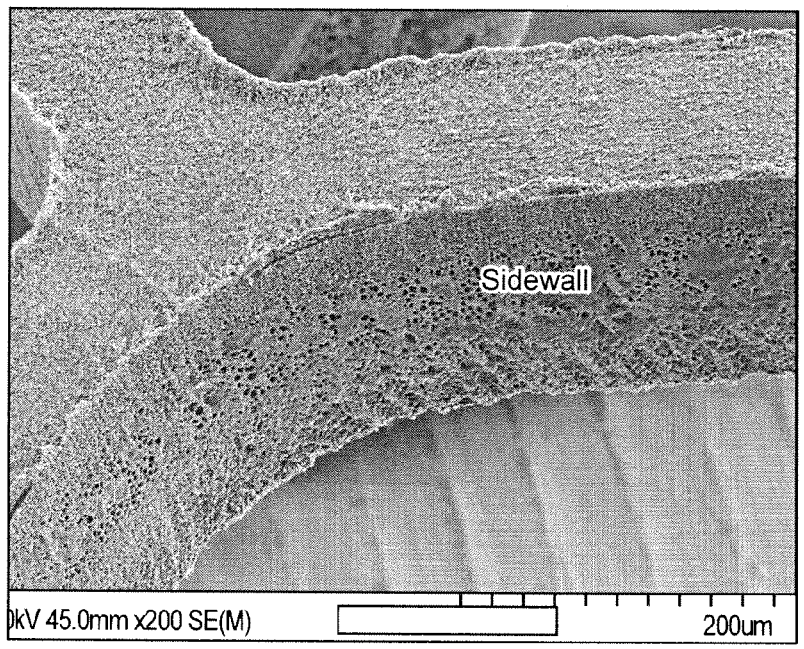
Figure 17:
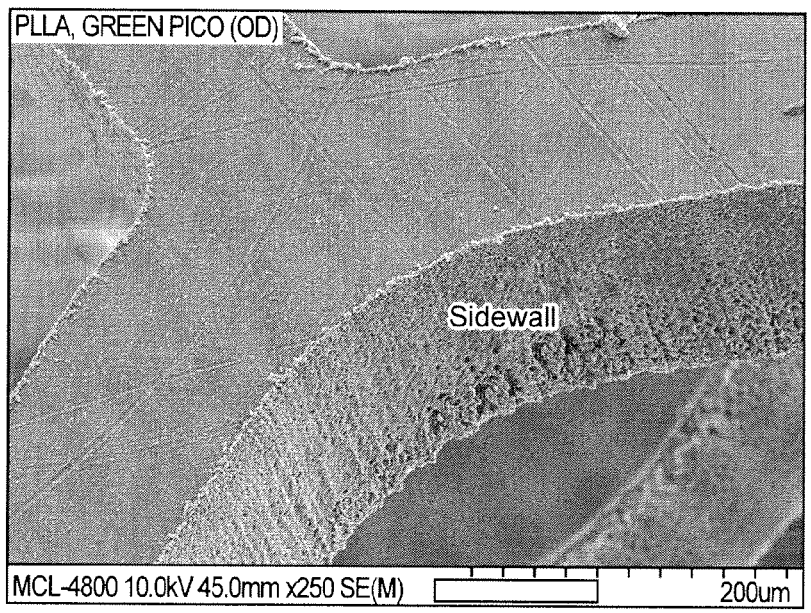

In addition, the modulus on the surface material of the stent (as a function of distance from the machined edge surface for the stents) was measured. Variation of modulus as a function of distance from the machined edge was observed. The variation becomes smaller as distance increases into the surface and tends to converge to the modulus of the virgin polymer not affected by the laser energy as shown in the FIG. 9. Additional testing on the mechanical properties of the affected region, including ultimate strength, elongation at break, elastic modulus, and maximum load were performed, and these mechanical outputs were adversely effected by the void formation.

The size of the voids and the depth to which they are present depend on laser parameters such as wavelength and pulse width. The size of the voids can be less than 1 micron, 1-2 microns, 2-5 microns, or greater than 5 microns. The cracks or voids may be present at no greater than 2 microns, 5, 10, 15, 20, or 30 microns. In general, polymer stent's mechanical properties are affected by those voids and cracks formation, but it can be alleviated by proper choice of laser parameters such as wavelength and pulse width.

Additionally, thermal and nonthermal damage to a substrate material depends on the laser energy for a given pulse width for at least two reasons. First, the optical penetration of the laser energy varies with wavelength. Second, the absorption coefficient, or more generally, the degree of absorption of laser energy by a lased polymer varies with wavelength. In general, the lower the absorption coefficient, at a given range of wavelength, the greater is the thermal effect on the substrate. For example, the absorption coefficient of PLLA increases from a negligible value at 800 nm to reach a maximum at about 300-320 nm. Thus, photochemical removal increases and thermal removal decreases as the wavelength decreases from about 800 nm to about 300-320 nm. Thus, the relative amount of nonthermal or thermal ablation also depends on the wavelength of the laser because the polymer absorption coefficient is dependent on the wavelength of the laser.

Therefore, the relative amount of nonthermal/thermal ablation depends on both the pulse width and the wavelength. Additionally, the degree of photochemical and thermal damage both depend on the pulse width.

As indicated above, the present invention includes adjusting parameters, such as pulse width and wavelength, to preserve or maintain mechanical properties of a stent and reduce or minimize damage to the uncut portion of the substrate. The adjusting can include selecting one or more wavelengths between ultraviolet (10-400 nm) and infrared (>700 nm) and one or more pulse widths. In some embodiments, a wavelength is selected such that the polymer has an absorption coefficient at the wavelength that is less than the maximum absorbance of the polymer, for example, the absorbance is 5-10%, 10-20%, 20-40%, or 40-60% of the maximum absorbance.

In some embodiments, the pulse width is adjusted for the one or more wavelengths to avoid excessive melting, even with an appropriate level of cooling during machining. Excessive melting may correspond to greater than 0.25, 0.5, or greater than 1 micron thickness of melting material.

For a given pulse width and wavelength, the average laser power or power (energy per pulse×repetition rate) and repetition rate selected in order to provide a fluence (energy per pulse/spot size of beam) that is high enough so that the beam cuts the substrate all the way through, for example, the wall of polymer tubing. The beam spot size is generally 10-20 microns, but can be less than 10 or greater than 20 microns depending on the application. A pulse energy and fluence (based on a 10 micron spot size) for laser cutting polymers can be 4-200 µJ and 0.5-200 $J/cm^2$, respectively. The average power per pulse of a beam can be 0.5-4 W or more than 4 W. More narrowly, the power can be 0.5-1 W, 1-1.5 W, 1.5-1.8 W, 1.8-2 W, 2-2.2 W, 2.2-2.5 W, 2.5-2.8 W, 2.8-3 W, 3-3.2 W, 3.2-3.5 W, 3.5-3.8 W, 3.8-4 W. For a 10 ps pulse width laser, the repetition rate can be 25-100 kHz, 25-50 kHz, 50-60 kHz, 60-80 kHz, or 80-100 kHz.

Additionally, the repetition rate and cooling gas flow rate (e.g., in SCFH He) are adjusted or selected in combination to reduce or minimize thermal effects (e.g., melting at surface of cut) and to maximize cutting speed. In general, the repetition rate and cutting speed are directly proportional, i.e., the faster the repetition rate, the faster the cutting speed, resulting in a lower process time per stent. However, as the repetition rate is increased, the thermal effects tend to increase. An increase in the cooling gas flow rate can mitigate the thermal effects from the increased repetition rate, allowing a higher repetition rate, and thus cutting speed. Thus, the repetition rate and cooling gas flow are chosen to obtain the fastest process time with acceptable thermal effects.

Although laser machining in a picosecond range, e.g., 1-12 ps or more, results in thermal effects, it may be advantageous to machine in this range since the thermal effects are more effectively controlled than photochemical effects. As indicated above, the thermal effects can be mitigated by cooling substrate as it is machined with a cooling gas.

Additionally or alternatively, minimizing the damage may correspond to minimizing the thickness of the affected region next to the laser machined edge that includes voids. For example, the thickness of the region can be between less than 2 microns, 5 microns, less than 20 microns, or less than 30 microns. The void region can be 1-2 microns, 2-5 microns, 2-10 microns, 2-20 microns, or 5-10 microns. Additionally or alternatively, minimizing damage can help minimize the modulus variation of the cut stent with distance in the damaged region. The parameters may be adjusted to obtain the fasting convergence of the modulus toward a modulus of an undamaged polymer. The modulus may converge at less than 4 microns, less than 8 microns, or less than 20 microns of the machined edge surface. The modulus may converge at between 1-4 microns, 4-8 microns, or 8-20 microns of the machined edge surface. The modulus may converge at 4 microns or less, 8 microns or less, 15 microns or less, or 20 microns or less from the machined edge surface.

Additionally or alternatively, damage may be minimized to the most desirable mechanical properties of the damaged region by adjusting the wavelength and pulse width, for example, the ultimate strength, elongation at break, elastic modulus, or maximum load. The most desirable is to have the cut polymer substrate maintaining the same properties prior to its laser machining.

The embodiments further include implementation a laser system and parameters in laser machining a PLLA substrate to manufacture a stent. In such embodiments, the laser wavelength may be in the visible light spectrum from 390 to 800 nm. In some embodiments, the laser wavelength is in the green spectrum or from about 496 to 570 nm, or more narrowly 532 nm or 515 nm. In some embodiments, the pulse width can be 0.8 ps or less, 0.8-1 ps, 1-5 ps, 5-10 ps, 10-12 ps, 12-15 ps, or greater than 15 ps. As disclosed in the examples, the inventors have demonstrated that ablating with a 10 ps laser with 532 nm wavelength at 80 kHz repetition rate provides minimal damage to the PLLA stent as compared to other combinations of wavelengths with lower pulse widths. In the green wavelength range or at 532 nm specifically, the repetition rate of the laser beam may be 25-100 kHz, or more narrowly, 25-40 kHz, 40-80 kHz, or 80-100 kHz. Table 1 provides laser parameter ranges used in the study.

TABLE 1

Laser parameters

| Description | Study range |
| --- | --- |
| Wavelength, nm | 532 nm |
| Polarization | circular |
| Average laser power, W | 1.5-3.0 |
| Pulse energy | 21 μJ |
| Pulse width | 12 ps |
| Repetition rate | 80 kHz for most stents |
| | 100 kHz for some tests |
| Gas (Helium) Flowrate, SCFH | 6 to 10 |
| Nozzle to substrate distance | 0.9 mm |
| Beam size | 8 mm |
| cutting speed, inch/min | 4 to 16 |

The following definitions apply herein:

All ranges include the endpoints and any value within the endpoints, unless otherwise specified.

"Radial strength" of a stent is defined as the pressure at which a stent experiences irrecoverable deformation.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

The "maximum load" or ultimate load is the absolute maximum load (force) that a structure can bear without failing.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus is the initial slope of a stress-strain curve, and therefore, determined by the linear Hookean region of the curve. For example, a material has both a tensile and a compressive modulus.

"Strain" refers to the amount of elongation or compression that occurs in a material at a given stress or load.

"Elongation" may be defined as the increase in length in a material which occurs when subjected to stress. It is typically expressed as a percentage of the original length.

"Elongation to Break" is the strain on a sample when it breaks. It is usually is expressed as a percent.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

The following set of examples describes results of laser machining stents from PLLA tubing for seven different parameter combinations of pulse width and wavelength. The PLLA tubing was formed from an extrusion process from 100% PLLA resin. The dimensions of the tubing, the extruded dimensions, are: outside diameter (OD)=0.0066 inch and inside diameter (ID)=0.0025 inch. The extruded PLLA tubes were radially expanded according to a process described previously, for example, in U.S. application Ser.

No. 12/554,589, which is incorporated by reference herein. The target percent radial expansion (% RE) was 400%, where % RE is deformed as 100%×(Inside Diameter of Expanded Tube/Original Inside Diameter of Tube−1).

The seven different parameter combinations of pulse width and wavelength are listed in Table 2.

TABLE 2

Pulse width and wavelength combination used to machine different sets of substrates

| Set No. | Pulse width | Wavelength (nm) | Laser |
|---|---|---|---|
| 1 | 10 ps | 355 | Trumpf[1] |
| 2 | 10 ps | 532 | Lumera[2] |
| 3 | 100 fs | 266 | Libra[3] |
| 4 | 100 fs | 400 | Libra[3] |
| 5 | 100 fs | 800 | Libra[3] |
| 6 | 800 fs | 1064 | IMRA[4] |
| 7 | 800 fs | 1550 | Raydiance[5] |

[1] Trumpf Laser Technology of Fremont, CA
[2] Lumera Laser GmbH of Kaiserslautern, Germany
[3] Coherent, Inc., Santa Clara, CA
[4] IMRA of Fremont, CA
[5] Raydiance of Petaluma, CA Additional laser parameters for the runs are given in Table 3. The speed is the translational rate of the beam across the surface of the substrate. The passes is the number of times the cut pattern is repeated. Processing time is the time required to cut an entire stent. The Coherent Libra (set #5) corresponds to the 800 nm in Table 3. The Pico (532 nm) lasers correspond to set #2. The lasers in Table 3 are fixed wavelength lasers.

TABLE 3

Summary of laser parameters

| Laser Parameters | Femto (800 nm) | Pico (355 nm) | Pico (532 nm) | Pico (532 nm) | Pico (532 nm) |
|---|---|---|---|---|---|
| Focusing Lens (mm) | 100 | 100 | 100 | 100 | 100 |
| Spot Size (micron) | 20 | 15 | 20 | 20 | 20 |
| Rep Rate (kHz) | 5 | 80 | 80 | 80 | 80 |
| Power (mW) | 160 | 200 | 1750 | 2100 | 2270 |
| Speed (in/min) | 4 | 10 | 4 | 8 | 16 |
| Passes | 1 | 2 | 1 | 1 | 1 |
| Helium (SCFH) | 7 | 6-8 | 7 | 10 | 9 |
| Processing time per stent (min:sec) | 6:34 | 5:20 | 6:34 | 3:17 | 1:39 |

The properties of the surface regions at the machined edge were assessed using several testing techniques. Techniques and the properties obtained from the tests are summarized in Table 4. Testing was performed on the samples using cryo ultra-microtome, nanoindentation, and tensile testing.

TABLE 4

Summary of test methods and properties studied

| Testing Method | Properties |
|---|---|
| Cryo-ultra microtome/SEM | Voids, cracks |
| Nanoindentation | Modulus vs. distance from cut surface |
| Tensile testing | Ultimate strength |
| | Elongation at break |
| | Elastic modulus |
| | Maximum load |

The cryo-ultra microtome refers to a technique of cutting ultrathin sections for microscopic examination. Thin sections of the machined stents normal to the machined edge were cut and examined with a scanning electron microscope (SEM). The depth and size of voids and cracks for the different sets were compared. Nanoindentation was used to measure the modulus of the substrate as a function of distance from the machined edge. Tensile testing was used to measure the mechanical properties of the surface region from dog-bone structures cut from along the machined edge.

Cryo-Ultra Microtome Results

A summary of the results of cryo-ultra microtome technique for four combinations of pulse width and wavelength are given in Table 5 and FIGS. 5-8 show the SEM images of the surface region adjacent to the machined surface for each combination in Table 5. For set #5, a pronounced photochemical effect is shown by bubbles extending to a depth of 20 µm. In set #4, the lower wavelength compared to set #5 appears to have mitigated the photochemical effect since the depth of the bubbles is significantly less than set #5, however, the size of the bubbles in set #4 are larger. Contrary to what may have been expected, there is a larger depth for set #4 since the penetration depth and the wavelength are inversely proportional.

TABLE 5

Summary of cryo-ultra microtome/SEM results

| Set No. | Pulse width/ wavelength | Observation | FIG. |
|---|---|---|---|
| 5 | 100 fs/800 nm | bubbles about 2 µm diameter 20 µm depth | 5 |
| 4 | 100 fs/400 nm | bubbles about 1 µm diameter 5 µm depth | 6 |
| 1 | 10 ps/355 nm | cracking and bubbles about 5 µm diameter 30 µm depth | 7 |
| 2 | 10 ps/532 nm | bubbles less than 1 µm diameter 2 µm depth | 8 |

For set #1, cracks are present to a depth of 30 µm. Set #2 has the least damage among the four setups; the depth and the size of the bubble formation are the lowest from all the test conditions.

Nanoindentation

A summary of the nanoindentation results with five combinations of pulse width and wavelength are given in Table 6 and FIGS. 9-13. The figures show the modulus vs. displacement into the surface of the machined edge for 16 samples for each combination. Of the three combinations with a pulse width of 100 fs, the 800 nm samples (set no. 5) show the fastest convergence. Of the two combinations at 10 ps, the 532 nm wavelength has significantly faster convergence of the modulus. A comparison of the 100 fs/800 nm and the 10 ps/532 nm results shows that the fastest convergence of the modulus overall is provided by the 10 ps/532 nm wavelength combination.

TABLE 6

Summary of nanoindentation results

| Set No. | Pulse width/ wavelength | Observation | FIG. |
|---|---|---|---|
| 5 | 100 fs/800 nm | converges at about 8 µm depth | 9 |
| 4 | 100 fs/400 nm | — | 10 |
| 3 | 100 fs/266 nm | — | 11 |
| 1 | 10 ps/355 nm | converges at about 20 µm depth | 12 |
| 2 | 10 ps/532 nm | converges at about 4 µm depth | 13 |

Tensile Testing

Tensile testing of surface regions of the machined edge was performed for samples machined with pulse width/wavelength combinations of 100 ps/800 nm and 10 ps/532 nm. The testing was performed using conventional tensile testing equipment on dog-bone shape samples prepared from surface regions of laser machined substrates. Test details for the 100 fs/800 nm sample and the 10 ps/532 sample are given in Tables 7 and 8, respectively.

TABLE 7

Description of tensile test sample using 100 fs/800 nm laser

| Samples | Longitudinal dog-bones |
| --- | --- |
| Rate | 0.1 in/min |
| Number of samples | 19 |
| Thickness | 0.0060 ± 0.0002 in. |
| Width | 0.0064 ± 0.0002 in. |

TABLE 8

Description of the tensile test sample using 10 ps/532 nm laser

| Samples | Longitudinal dog-bones |
| --- | --- |
| Rate | 0.1 in/min |
| Number of samples | 16 |
| Thickness | 0.0061 ± 0.0001 in. |
| Width | 0.0060 ± 0.0001 in. |

Table 9 summarizes the tensile test results. The most remarkable property difference is the elongation at break. The 10 ps/532 nm samples had an elongation more than 2.5 times or about 60% larger than the 100 fs/800 nm samples. Therefore, the former samples have a significantly higher fracture resistance.

TABLE 9

Summary of tensile test results

| Property | 100 fs/800 nm | 10 ps/532 nm | Percent difference* |
| --- | --- | --- | --- |
| Ultimate Strength (ksi) | 12.5 ± 0.7 | 15.5 ± 0.9 | 19 |
| Elongation (plastic) (%) | 196 ± 66 | 496 ± 54 | 60 |
| Elastic Modulus (ksi) | 58 ± 4 | 65 ± 3 | 11 |
| Max. Load (lb$_f$) | 0.49 ± 0.03 | 0.57 ± 0.04 | 14 |

*100% × (3rd col. property − 2nd col. property)/3rd col. property

Summary of Material Results

A summary of the material results for the sets of samples is provided in Table 10.

The 10 ps/532 samples have the best properties.

TABLE 10

Summary of testing results.

|  | 100 ps/800 nm | 10 ps/355 nm | 10 ps/532 nm |
| --- | --- | --- | --- |
| Cryo-Ultra microtome | 20 um depth, 2 μm dia | 30 um depth, 5 μm dia | 2 um deep, <1 μm dia |
| Nano Indentation | Converge @ 8 μm | Converge @ ~20 μm | Converge @ 4 μm |
| Tensile testing | UTS 12.5 ksi, 196% elongation | — | UTS 15.5 ksi, 496% elongation |

Quality of Machined Edge

The quality of the machined edge was investigated through observation of SEM images of the sidewalls. One of the causes of roughness is redeposition of vaporized substrate material. FIGS. 14-17 depict SEM images showing the sidewalls of stents machined with 100 fs/800 nm, 100 fs/400 nm, 10 ps/355 nm, and 10 ps/532 nm, respectively. The sidewall machined with the 10 ps/532 combination has the smoothest machined edge.

The above examples indicate that the 532 nm wavelength provides the best balance of cutting speeds with thermal effects and photochemical effects. This method can be applied to poly(L-lactide-co-glycolide) with any molar ratios of L-lactide to glycolide between 0 and 1. The laser system and its settings can also be applied to cut metallic substrates such as Ta—Nb—W, and Co—Cr alloys.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A polymer stent, comprising:
a plurality of interconnected structural elements formed by laser machining a polymer substrate made of a polymer with a laser beam that cuts through a wall of the polymer substrate to form the structural elements,
wherein the structural elements have sidewalls corresponding to laser machined edge surfaces between an outer surface and inner surface of the polymer substrate formed when the laser beam cuts through the wall of the polymer substrate,
wherein the structural elements comprise bends or crowns that undergo stress and strain when the stent is crimped and deployed and structural elements connecting the bends or crowns,
wherein a surface region adjacent to the sidewalls of the bends or crowns and the structural elements connecting the bends or crowns has damage caused by interaction of the laser beam with the substrate, characterized in that
wherein the damage comprises voids or cracks dispersed in the surface region to a depth of 2 microns or less from the sidewalls corresponding to the laser machined edge surfaces.

2. The stent of claim 1, wherein the damage further comprises variation in a modulus of the polymer with distance from the laser machined edge surfaces, wherein the modulus converges at a distance no greater than 5 microns.

3. The stent of claim 1, wherein the polymer is poly(L-lactide) or poly(L-lactide-co-glycolide).

4. The stent of claim 1, wherein the polymer is a copolymer including poly(L-lactide).

5. The stent of claim 1, wherein a size of the voids is less than 1 micron.

6. A stent, comprising:
a plurality of interconnected structural elements formed by laser machining a polymer substrate made of a polymer with a laser beam from a laser with a pulse width and wavelength that cuts through a wall of the substrate to form the structural elements having sidewalls corresponding to laser machined edge surfaces,
wherein the structural elements comprise bends or crowns that undergo stress and strain when the stent is crimped and deployed and structural elements connecting the bends or crowns,
wherein the laser beam modifies the substrate in a surface region adjacent to the laser machined edge surfaces of the bends or crowns and structural elements connecting the bends or crowns to include voids, cracks, and variation in modulus of the polymer with distance from the sidewalls corresponding to the laser machined edge surfaces, or a combination thereof, wherein a pulse width and wavelength of the laser are selected so that the voids or cracks are present at no greater than a depth of 2 microns or the modulus converges at no greater than 4 microns.

7. The stent of claim 6, wherein the polymer is poly(L-lactide) or poly(L-lactide-co-glycolide).

8. The stent of claim 6, wherein the polymer is a copolymer including poly(L-lactide).

9. The stent of claim 6, wherein a size of the voids is less than 1 micron.

10. A stent comprising:
a plurality of interconnected structural elements formed by laser machining a polymer substrate made of a polymer with a laser beam to cut through a wall of the substrate to form structural elements having a machined edge surface, wherein the structural elements comprise bends or crowns that undergo stress and strain when the stent is crimped and deployed and structural elements connecting the crowns; and wherein interaction of the laser beam with the substrate causes damage in a surface region adjacent to the machined edge surface of the bends or crowns and structural elements connecting the bends or crowns arising from thermal and nonthermal ablation, wherein the damage comprises of cracks or voids no greater than a depth of 2 microns arising from nonthermal ablation and melting no greater than 1 micron in thickness arising from thermal ablation.

11. The stent of claim 10, wherein the polymer is poly(L-lactide) or poly(L-lactide-co-glycolide).

12. The stent of claim 10, wherein the polymer is a copolymer including poly(L-lactide).

13. The stent of claim 10, wherein a size of the voids is less than 1 micron.

* * * * *